(12) United States Patent
Wall et al.

(10) Patent No.: US 8,491,588 B2
(45) Date of Patent: Jul. 23, 2013

(54) SURGICAL INSTRUMENT FOR SECURING A SPINAL ROD

(75) Inventors: Daniel Paxton Wall, Medina, TN (US); Richard Quinn Brown, Collierville, TN (US)

(73) Assignee: Warsaw Orthopedic, Inc., Warsaw, IN (US)

( * ) Notice: Subject to any disclaimer, the term of this patent is extended or adjusted under 35 U.S.C. 154(b) by 20 days.

(21) Appl. No.: 13/159,151

(22) Filed: Jun. 13, 2011

(65) Prior Publication Data

US 2012/0316609 A1 Dec. 13, 2012

(51) Int. Cl.
*A61B 17/70* (2006.01)

(52) U.S. Cl.
USPC .......................... 606/86 A; 606/105; 606/104

(58) Field of Classification Search
USPC . 606/86 A, 105, 205–209, 104, 99; 81/177.2, 81/427.5, 415, 416, 177.7; 269/3, 6, 95; 29/278, 29/255; 403/160; 909/914, 916
See application file for complete search history.

(56) References Cited

U.S. PATENT DOCUMENTS

| | | | |
|---|---|---|---|
| 7,073,415 B2 | 7/2006 | Casutt et al. | |
| 7,686,814 B2 * | 3/2010 | Lim et al. | 606/105 |
| 8,070,751 B2 * | 12/2011 | Justis et al. | 606/86 A |
| 8,075,565 B2 * | 12/2011 | Wilcox et al. | 606/86 A |
| 2004/0267279 A1 * | 12/2004 | Casutt et al. | 606/104 |
| 2005/0245928 A1 * | 11/2005 | Colleran et al. | 606/61 |
| 2008/0119862 A1 | 5/2008 | Wicker et al. | |
| 2010/0069972 A1 * | 3/2010 | Jones et al. | 606/86 A |

* cited by examiner

*Primary Examiner* — Jan Christopher Merene

(57) ABSTRACT

A surgical instrument for assembling a spinal rod to a plurality of anchoring members includes first and second levers that are pivotally, and optionally removably, connected for rotation about a pivot axis. The first lever has a hollow guide tube forming a first handle section and a first distal end section, with a first longitudinal bore extending therethrough. The second lever has a second handle section, a second distal end section, and an intervening second intermediate section that interconnects the two in offset fashion. The second distal end section has a second longitudinal bore. The longitudinal bores accept bone anchor heads. Pivoting of the levers relative to each other about the pivot axis causes the bone anchors to move toward or away from each other. The first and second bores may be configured to mate with bone screw assemblies having extended tabs.

20 Claims, 11 Drawing Sheets

SURGICAL INSTRUMENT FOR SECURING A SPINAL ROD

BACKGROUND

The invention relates to an instrument and related method for securing a spinal rod during a surgical procedure.

Spinal implants are often inserted into a patient's body in order to stabilize an internal structure, promote healing, or relieve pain. For example, a common procedure involves the use of anchoring members, such as pedicle screws or hooks, joined by a flexible or rigid spinal rod in order to secure vertebrae in a desired position. Once the spinal rod is placed in the patient's body, the spinal rod should be firmly secured to the relevant anchoring members. Typically, this securing is achieved by rotating a set screw or other locking element to clamp the spinal rod, directly or indirectly, against the relevant anchoring element. However, the application of the necessary rotational force to the locking element tends to likewise apply an undesirable rotational force to the anchoring element. As such, some surgical methods involve the use of a guide tube that couples to the anchoring element. A driving tool is inserted through the guide tube and mates with the locking element. Then, when the tightening torque is applied to the locking element, the guide tube provides a means of applying a suitable counter-torque to the anchoring element.

Further, a surgeon often desires to distract or compress the relevant vertebrae when the spinal rod is secured in place, so that the spinal rod may help hold the vertebrae in a desired position. Typically, this is achieved by using a separate surgical distraction or compression instrument that must access the surgical site while the spinal rod is being secured as described above. The use of the separate tool may present complications during the spinal rod securing process.

While a number of specialized tools have been developed to facilitate the placement of spinal prostheses, including guide tubes and separate distractor/compressor tools, there remains a need for alternative surgical instrumentation, advantageously surgical instrumentation that is well suited to use during minimally invasive procedures.

SUMMARY

In some embodiments, the present invention provides a surgical instrument for assembling a spinal rod to a plurality of anchoring members (e.g., polyaxial bone screws). The instrument includes first and second levers that are pivotally connected for relative rotation about a pivot axis. The first lever comprises a hollow guide tube extending along a first longitudinal axis from a first proximal handle section to a first distal end section. The guide tube has a first longitudinal bore extending therethrough along the first axis. The first lever also has a first intermediate section disposed between the first handle section and the first distal end section. The second lever has a second proximal handle section, a second distal end section, and an intervening second intermediate section. The second handle section extends along a second longitudinal axis. The second distal end section extends along a third longitudinal axis. The second and third axes are non-parallel. The second distal end section has a second longitudinal bore extending along the third axis. The first and second levers are pivotally connected at the first and second intermediate sections for relative rotation about the pivot axis. The first and second axes extend in a common first plane. The pivot axis is transverse to the first plane at a non-perpendicular first angle, and the third axis is transverse to the first plane at a non-perpendicular second angle. Pivoting of the second lever relative to the first lever about the pivot axis causes the second proximal end section to traverse along the first plane. The first and second levers may be removably and pivotally connected. The first and second bores may be configured to mate with bone screw assemblies having extended tabs. The second intermediate section may include a curvate section that links the second distal end section to the second handle section in offset fashion. The first and third axes may intersect the pivot axis, with the second axis skew relative to the pivot axis. The surgical instrument may be coupled to a spinal rod at the first and second distal end sections, with the spinal rod having a curvate longitudinal axis with a curvature generally centered on the pivot axis.

In other embodiments, the present invention provides a surgical instrument having first and second levers that are pivotally connected for relative rotation about a pivot axis, with the connection being releasable in some advantageous embodiments. The first lever includes a hollow guide tube extending along a first longitudinal axis from a first proximal handle section to a first distal end section. The guide tube has a first longitudinal bore extending therethrough along the first axis. The first lever further has a first intermediate section disposed between the first handle section and the first distal end section. The second lever has a second proximal handle section, a second distal end section, and an intervening second intermediate section. The second handle section extends along a second longitudinal axis. The second distal end section extends along a third longitudinal axis. The second and third axes are non-parallel. The second distal end section has a second longitudinal bore extending along the third axis. The first and second levers are pivotally connected at the first and second intermediate sections for relative rotation about a pivot axis. The pivot axis is non-perpendicularly transverse to the first axis. The instrument is configured such that when viewed normal to a plane defined by the first axis and the pivot axis: 1) the first and third axes proximally diverge; and 2) the first and second axes are parallel.

In other embodiments, the present invention provides a method of assembling a spinal rod to a plurality of anchoring members comprising: affixing a spinal rod at a first bone anchor anchored to a first vertebra; engaging a first lever with a first bone anchor anchored to a first vertebra; and engaging a second lever with a second bone screw anchored to a second vertebra. The first lever includes a hollow guide tube extending along a first longitudinal axis from a first proximal handle section to a first distal end section. The guide tube has a first longitudinal bore extending therethrough along the first axis; the first lever also has a first intermediate section disposed between the first handle section and the first distal end section. The second lever has a second proximal handle section, a second distal end section, and an intervening second intermediate section. The second handle section extends along a second longitudinal axis. The second distal end section extends along a third longitudinal axis. The second and third axes are non-parallel. The method also includes removably coupling the second lever to the first lever at the first and second intermediate sections for relative rotation about a pivot axis, with the pivot axis non-perpendicularly transverse to the first axis. Thereafter, the first and second bone anchors are moved closer together by rotating the first lever relative to the second lever about the pivot axis. While the first and second bone anchors are disposed closer together, the method includes affixing a spinal rod at the both the first and second bone anchors by tightening a fastener via the first or second bores. Thereafter, the first and second levers are decoupled from each other and removed from the first and second bone anchors.

Various aspects and embodiments are disclosed, which may be used alone or in any combination.

DETAILED DESCRIPTION

Figure 1:
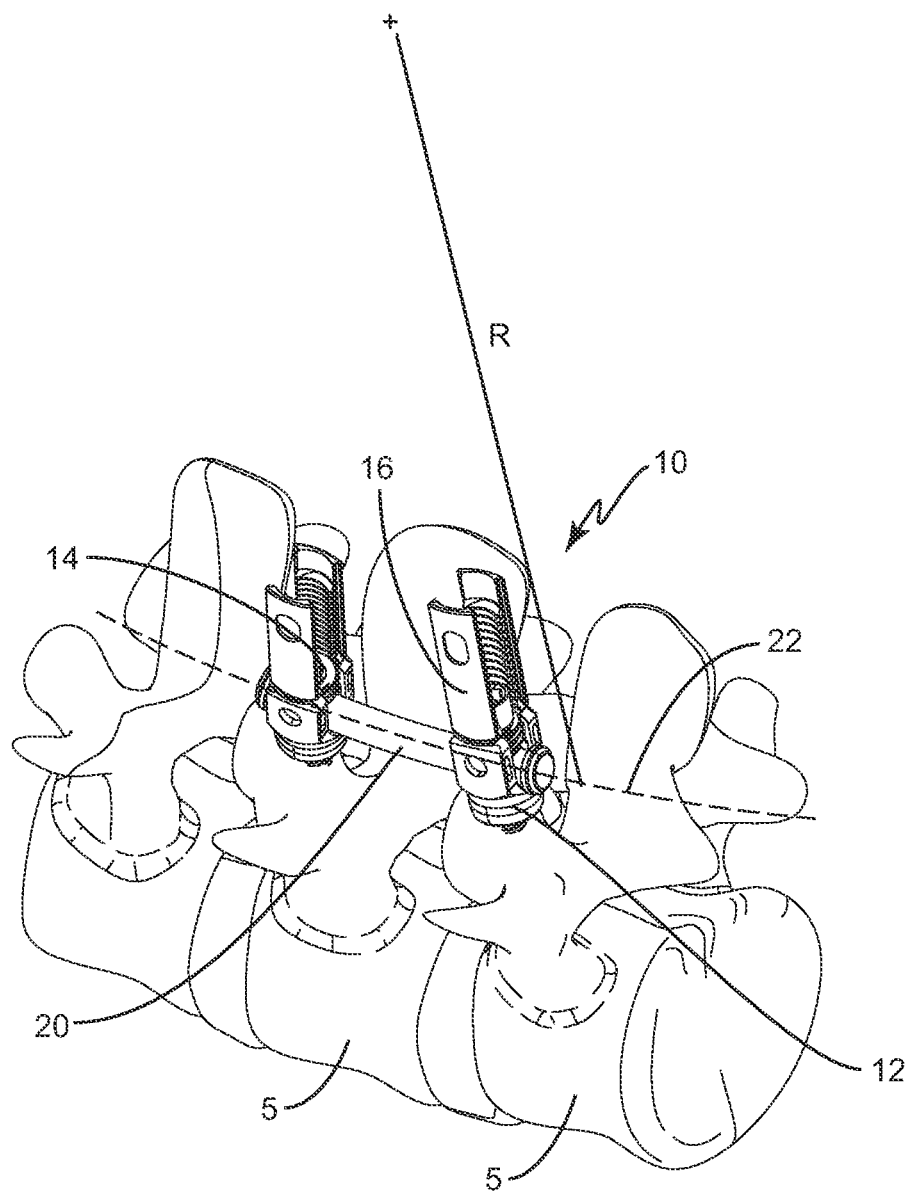
FIG. 1 shows a spinal rod and associated bone screw assemblies on the associated vertebrae, before removal of the associated extended tabs.

Illustrative embodiments of the present invention include a surgical instrument and/or a method of using a surgical instrument in association with the insertion of a spinal prosthesis 20. One common example of such a spinal prosthesis 20 is a rigid spinal rod. As such, the discussion below uses a rigid spinal rod as an illustrative example of a spinal prosthesis 20. The particular spinal rod 20 used for illustrative purposes is generally elongate along longitudinal rod axis 22. Rod axis 22 is typically a continuous curve with a relatively constant radius of curvature R. The end sections of rod 20 are typically mated to conventional polyaxial pedicle screw assemblies 10, which are in turn mated to the relevant vertebrae 5. The spinal rod 20 may be secured to the pedicle screws by clamping the rod 20 to the head 12 of the pedicle screw assembly via a set screw other locking element 14. For further information, attention is directed to U.S. Patent Application Publication 2005/0171540. However, it should be understood that the present invention is not limited to use with the particular spinal rod 20 shown, and may instead be used with any suitable spinal prosthesis.

Figure 2:
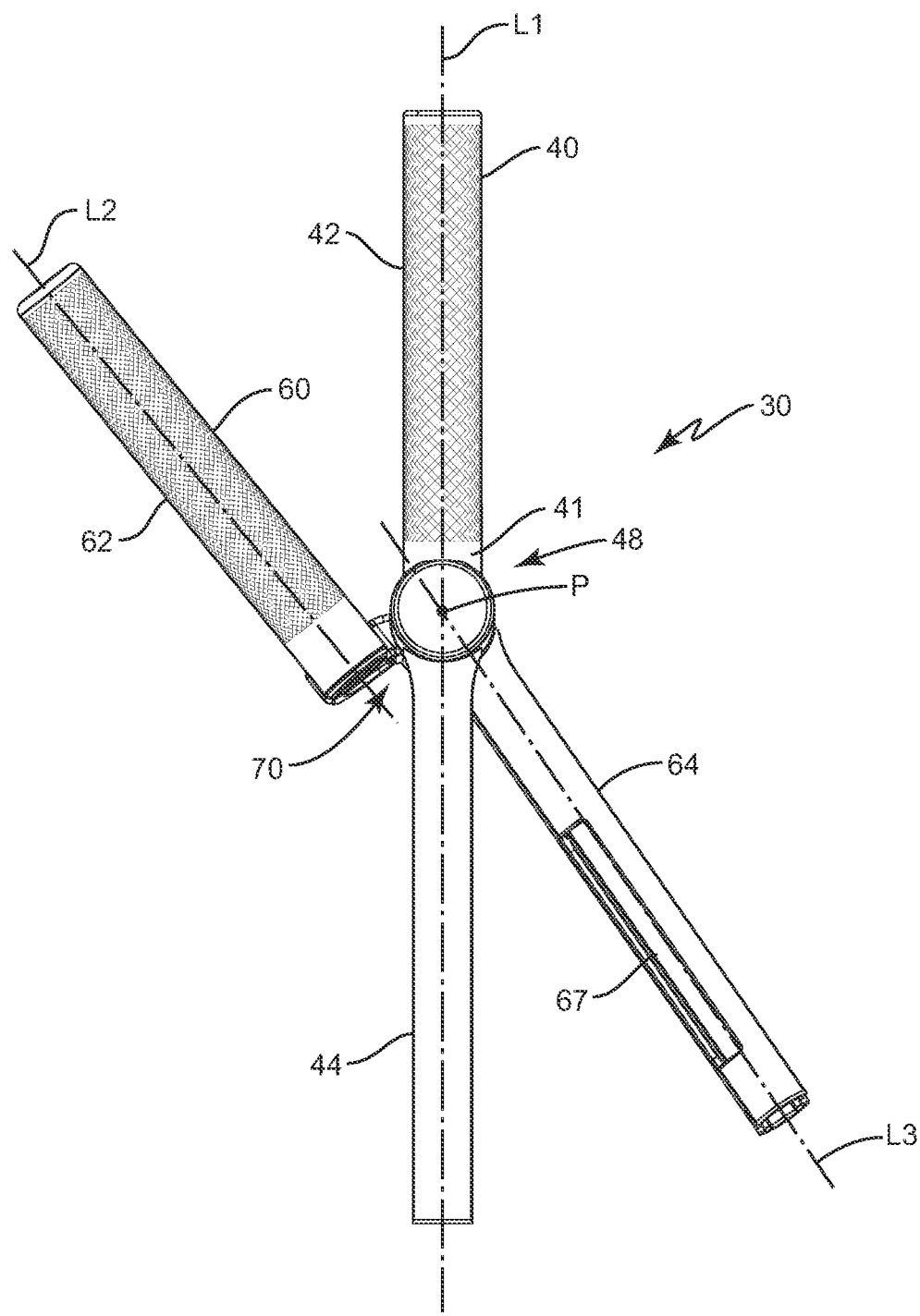
FIG. 2 shows a lateral view of a surgical instrument according to one embodiment of the present invention.

The instrument according to one embodiment is shown in FIG. 2, and generally indicated at 30. The instrument 30 includes two levers 40,60 that are pivotally connected together, and optionally removably connected together when assembled. The levers 40,60 advantageously provide a means for guiding a tightening tool 28 and providing a counter-torque to the tightening torque when securing a locking element 14 of a bone screw assembly 10. In some embodiments, the tightening tool 28 is inserted through one or the other lever 40,60 to tighten the locking element 14. Further, the levers 40,60 are pivotally connected, and are therefore also able to provide a distraction or compression force if desired.

Figure 3:
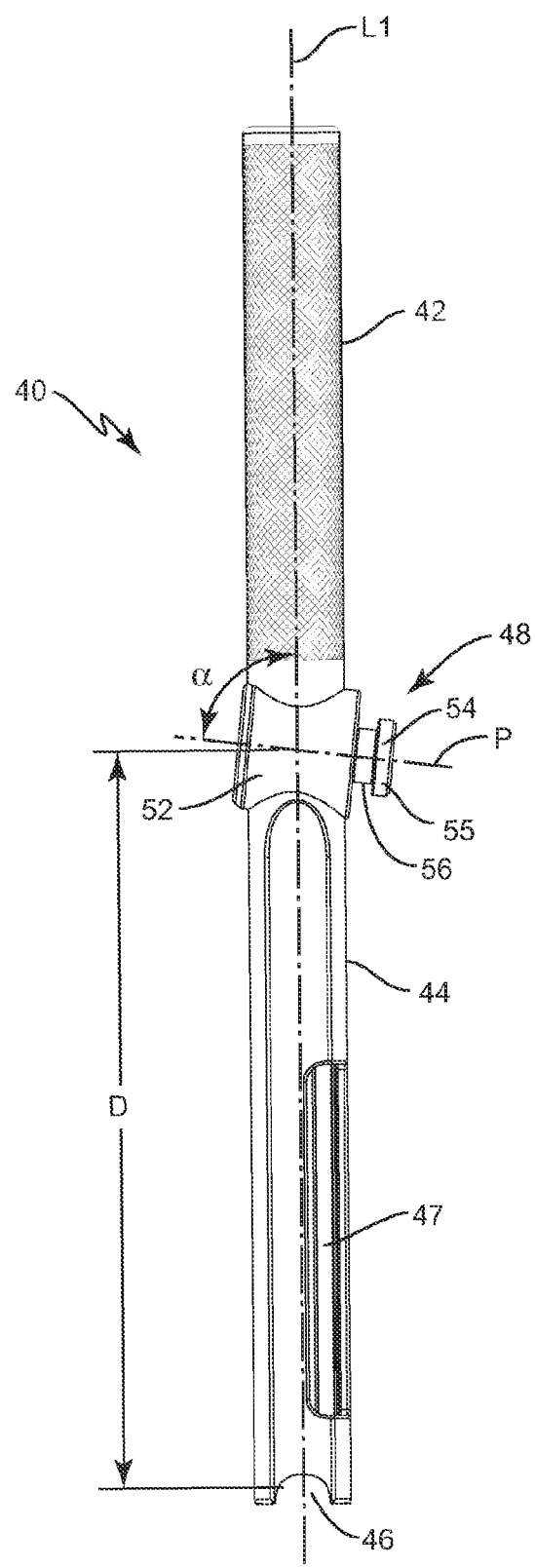
FIG. 3 shows one view of the superior lever of the device of FIG. 2, from the perspective of the inferior lever of FIG. 2.
Figure 4:
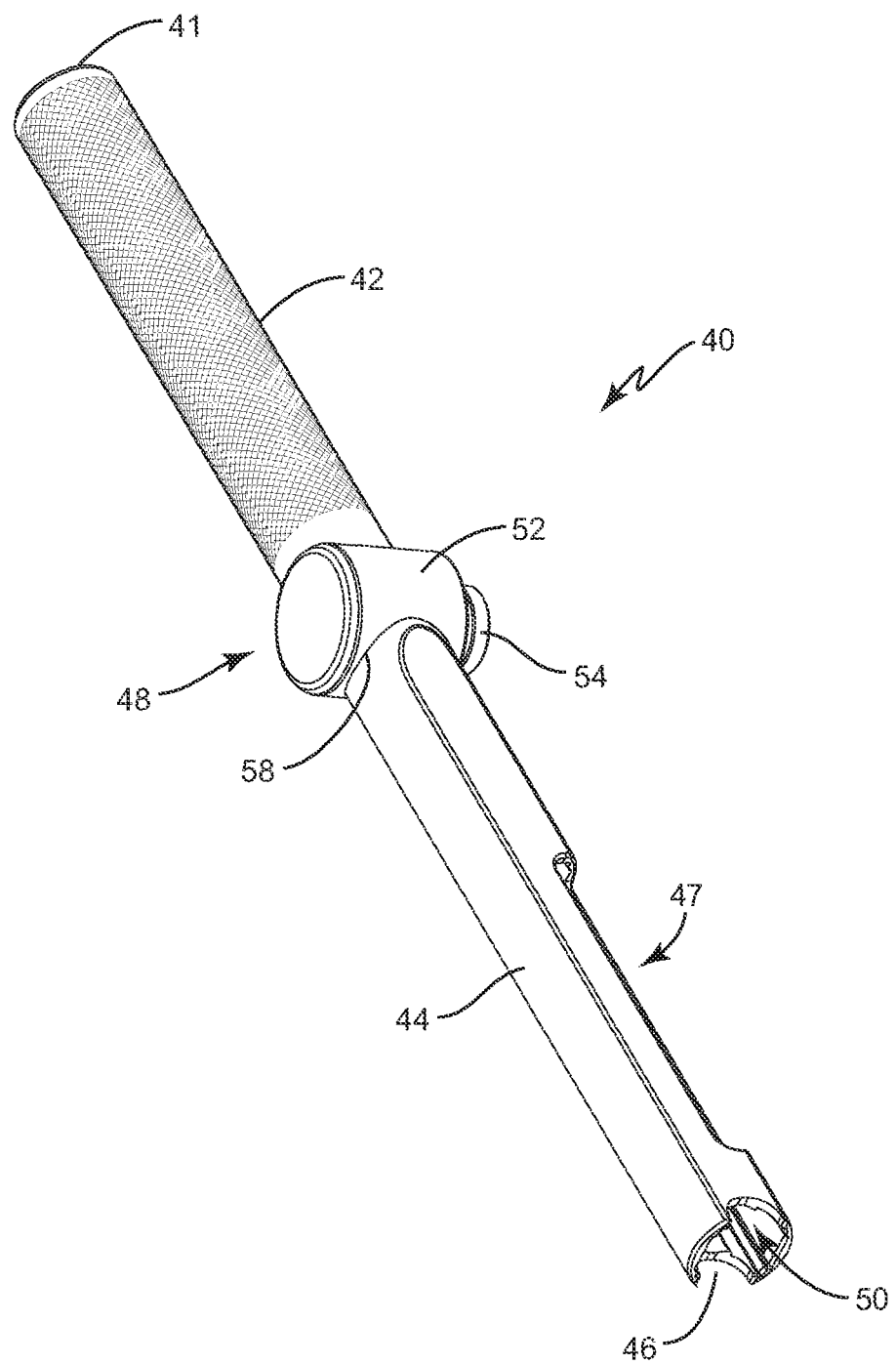
FIG. 4 shows another view of the superior lever of the device of FIG. 2.
Figure 5:
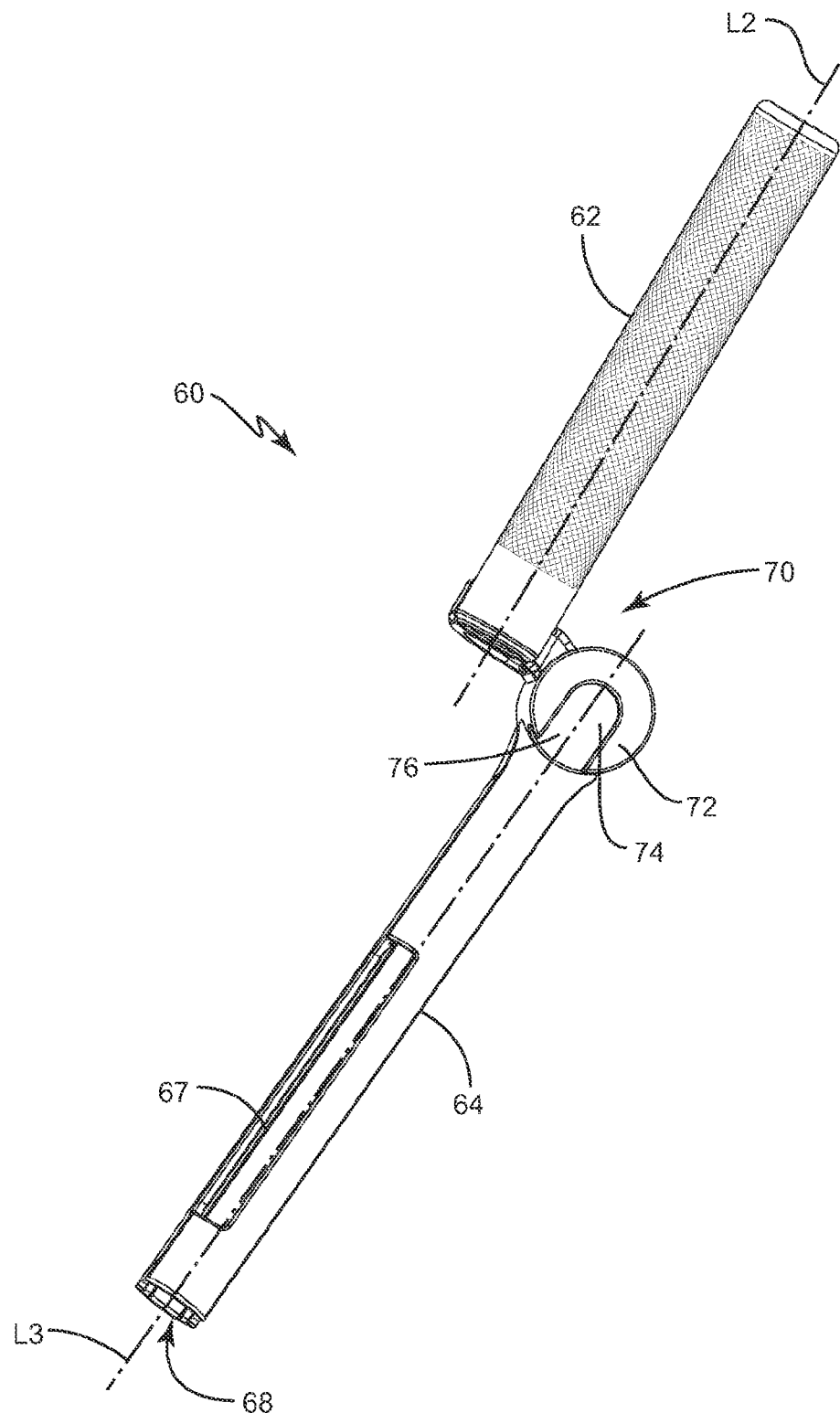
FIG. 5 shows one view of the inferior lever of the device of FIG. 2 from the perspective of the superior lever of FIG. 2.
Figure 6:
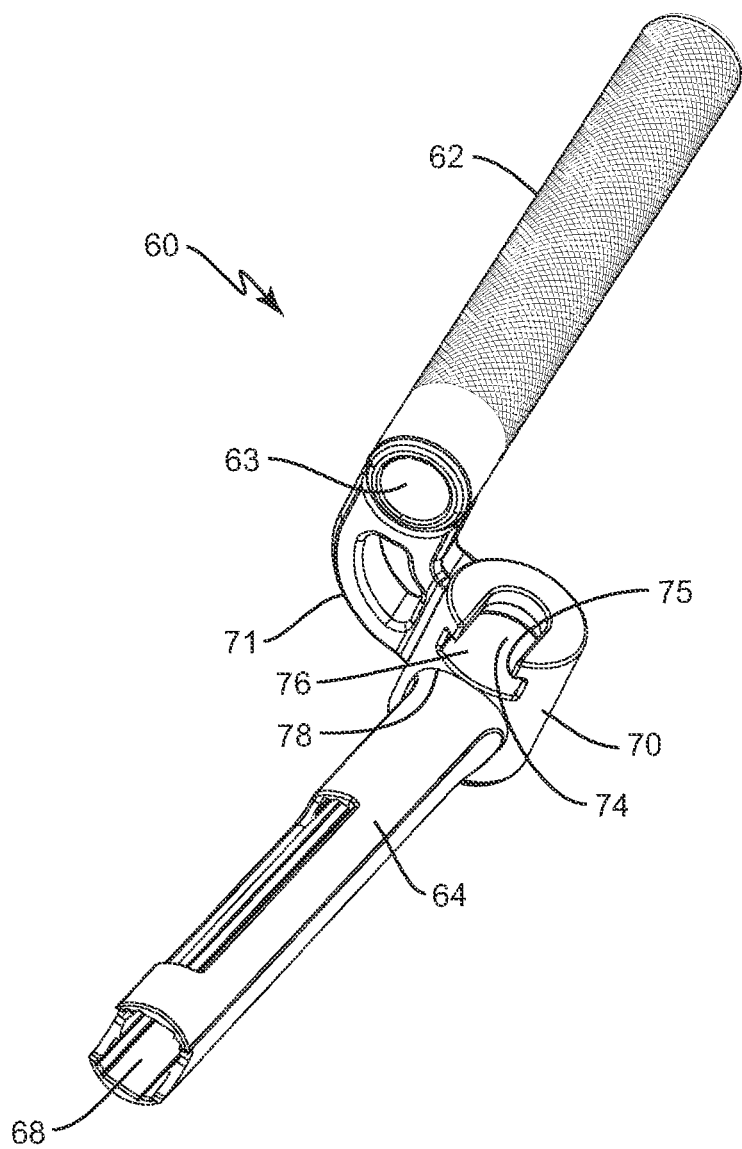
FIG. 6 shows another view of the inferior lever of the device of FIG. 2.
Figure 7:
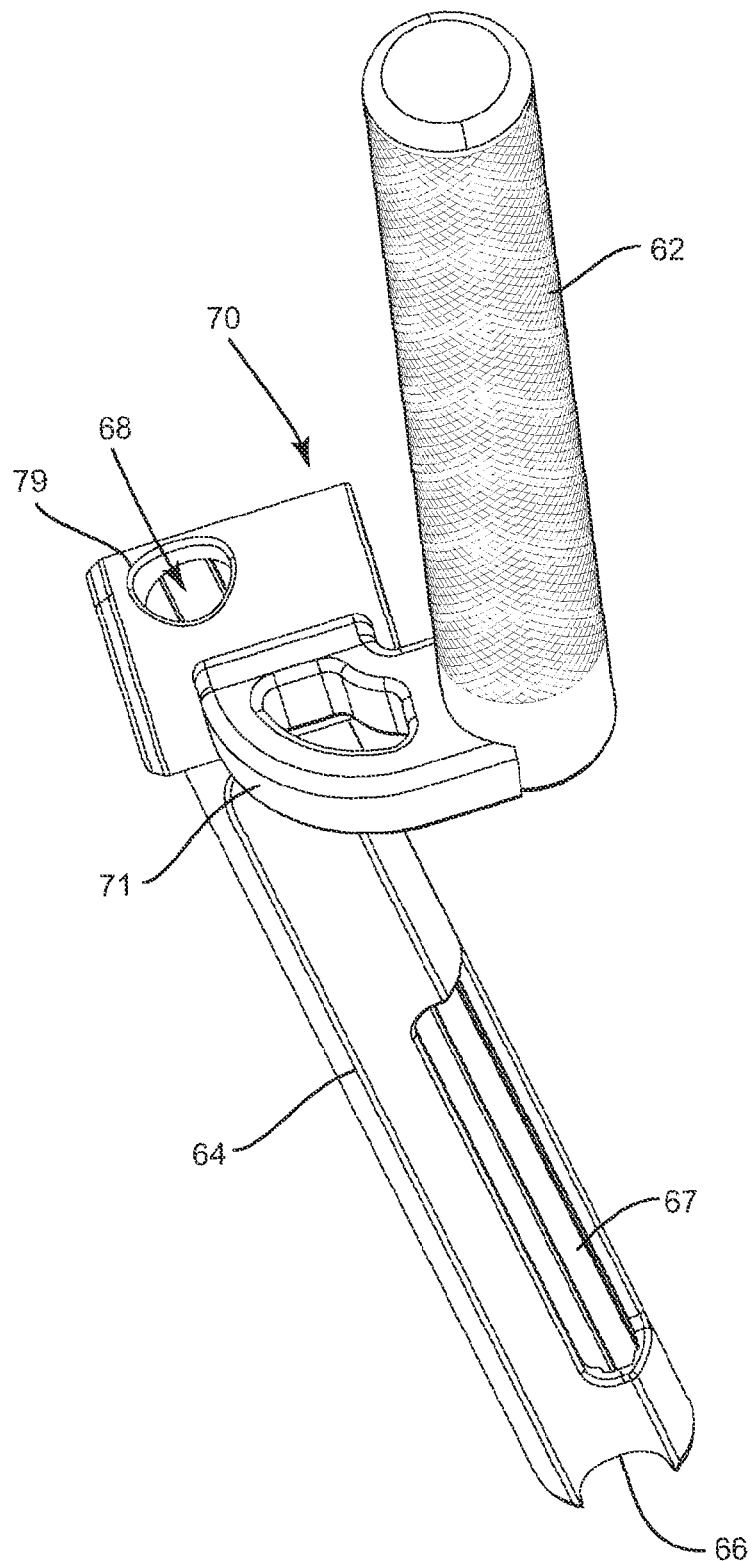
FIG. 7 shows another view of the inferior lever of the device of FIG. 2.

Lever 40 includes a hollow guide tube 41 and a mounting block 52. See FIGS. 2-5. The guide tube 41 includes a proximal handle section 42, a distal engaging section 44, and an intervening intermediate section 48. The guide tube 41 is advantageously straight with a central bore 50 that extends therethrough along the longitudinal axis L1 of the guide tube 41. Bore 50 may have circular or non-circular cross sections, as is desired. The handle section 42 advantageously has a textured outer surface (e.g., knurled) for improved grip by the surgeon. The distal engaging section 44 includes end notches 46 that cut transversely across the endface of the guide tube 41 perpendicular to axis L1. The notches 46 are advantageously generally U-shaped and are intended to receive the rod 20, as described further below. The distal engaging section 44 may also include suitable viewing port(s) 47 as desired; these view ports 47 may act as reliefs that allow the levers 40,60 to pivot closer together in some situations, as discussed further below. The mounting block 52 is affixed to guide tube 41 at intermediate section 48. The mounting block 52 may be generally cylindrical, with a transverse passage 58 to allow guide tube 41 to pass therethrough. The mounting block 52 includes a post-like protrusion 54 that extends in a direction generally away from guide tube 41 toward lever 60. The post 54 includes a head 55 that is enlarged relative to a neck 56 that connects to the main portion of mounting block 52. The post 54 advantageously has a cylindrical perimeter, as post 54 forms a portion of a rotatable coupling that couples lever 60 to lever 40 for rotation about a pivot axis P formed by post 54. It should be noted that the pivot axis P formed by post 54 intersects axis L1 at a non-perpendicular angle α (FIG. 3); thus, the pivot axis P may be described as being canted relative to axis L1. In some embodiments, angle α may be approximately 85°, such as about 84°.

Lever 60 includes a proximal handle section 62, a distal engaging section 64, and an intervening intermediate section 70. The handle section 62 is elongate along its longitudinal axis L2. The handle section 62 may include a bore 63, if desired, that extends along axis L2. As with handle section 42, handle section 62 advantageously has a textured outer surface (e.g., knurled) for improved grip by the surgeon. The distal engaging section 64 is elongate along its longitudinal axis L3. The distal engaging section 64 advantageously has a bore 68 extending therethrough along axis L3. Bore 68 may have circular or non-circular cross sections, as is desired. In some embodiments, bore 68 may not extend through distal engaging section, but may stop partway so that the upper end of distal engaging section 64 is not open. The distal engaging section 64 includes end notches 66 that cut transversely across the endface of the distal engaging section 64 perpendicular to axis L3. Like notches 46, notches 66 are advantageously generally U-shaped. The distal engaging section 64 may also include suitable viewing port(s) 67 as desired; these view ports 67 may act as reliefs that allow the levers 40,60 to pivot closer together in some situations, as discussed further below. Intermediate section 70 fixedly couples handle section 62 to distal engaging section 64 in offset or non-linear fashion. The intermediate section 70 includes a mounting block 72 and an offsetting flange 71. Mounting block 72 may advantageously be generally cylindrical. The endface of mounting block 72 facing lever 40 includes a recess 74 configured to accept post 54 of mounting block 52. The recess 74 advantageously includes an enlarged section disposed inboard of a lip 75. The recess 74 extends into mounting block 72 along pivot axis P, and is advantageously symmetric about pivot axis P except for channel 76. Recess 74 advantageously does not extend into the projected cross-section of distal engaging section 64 projected along axis L3; thus, recess 74 is laterally offset from distal engaging section 64. Channel 76 extends radially outward from recess 74 to the exterior of mounting block 72, and is advantageously aligned with axis 73. The channel 76 is sized to accept the neck 56 of post 54 so that post 54 may be slid radially inward into recess 74. Mounting block 72 also includes a passage 78 for receiving the distal engaging section 64. If distal engaging section 64 does not extend entirely through mounting block 72, mounting block 72 may include a suitable hole 79 for allowing access to bore 68 so that tightening tool 28 may be inserted into bore 68. Distal engaging section 64 is advantageously disposed so that axis L3 intersects pivot axis P at a non-perpendicular angle, so that distal engaging section 64 is tilted relative to pivot axis P. Flange 71 fixedly connects mounting block 72 to handle section 62, such that axis L2 is skew to pivot axis P and axis L3. Flange 71 is advantageously generally curvate as shown.

Figure 8:
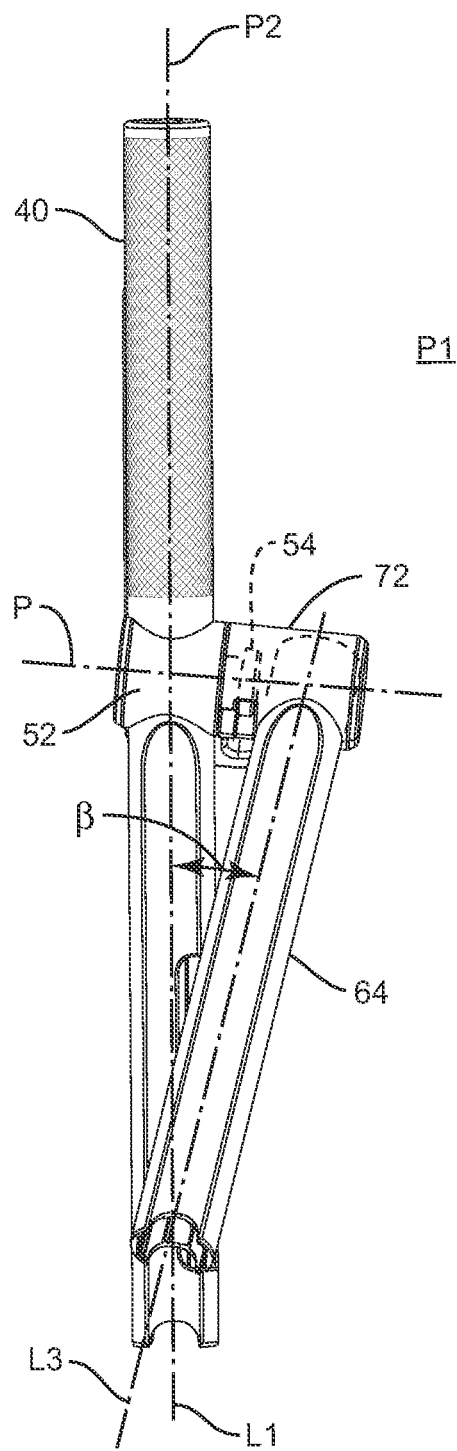
FIG. 8 shows a view of the surgical instrument of FIG. 2 taken normal to the plane P1.
Figure 9:
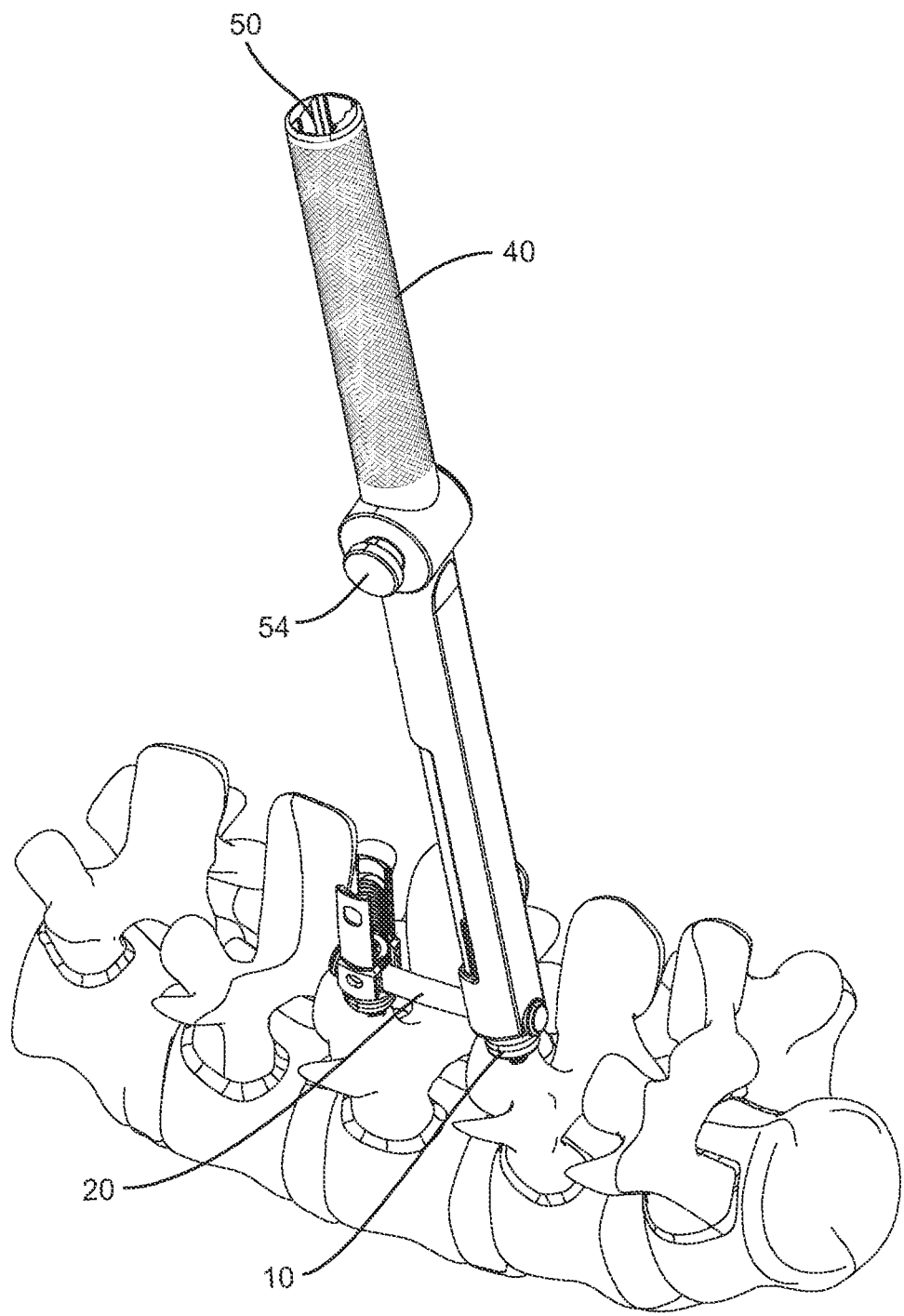
FIG. 9 shows the superior lever of FIG. 3 engaged with a spinal rod and a bone anchor.
Figure 10:
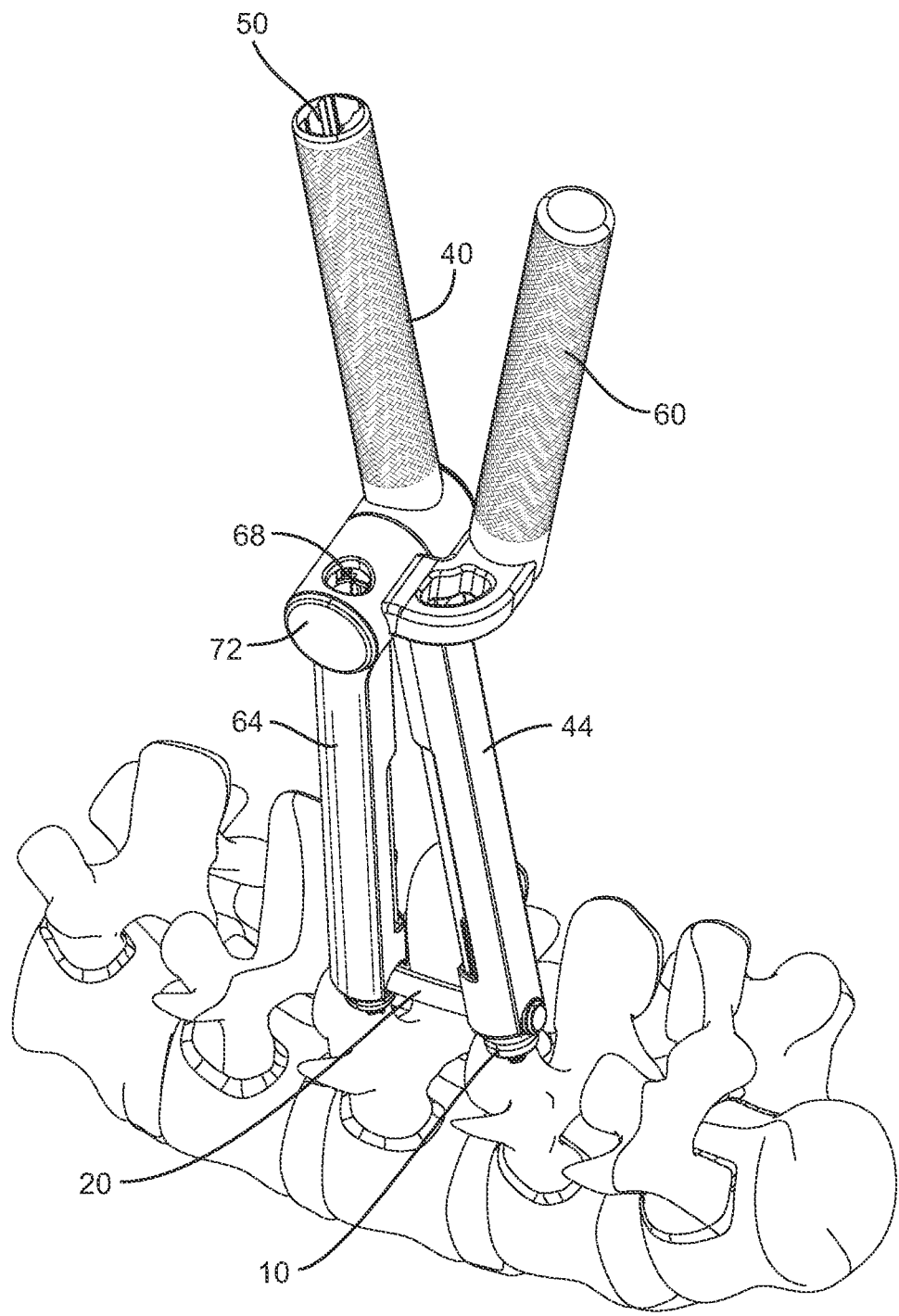
FIG. 10 shows the inferior lever of FIG. 5 added to the assembly of FIG. 9.
Figure 11:
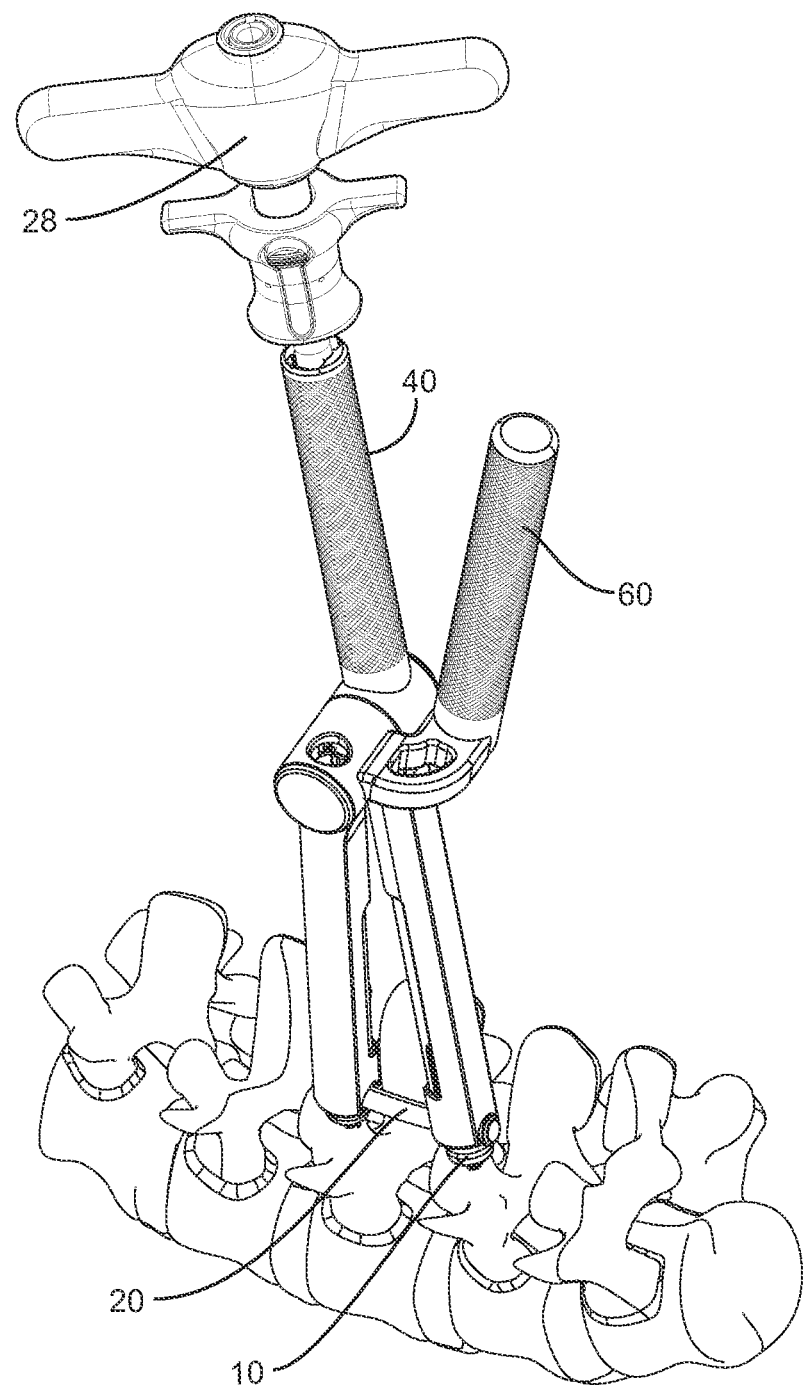
FIG. 11 shows a tightening tool inserted into the superior level for tightening the associated setscrew.

Lever 60 may be removably and pivotally mounted to lever 40 by sliding neck 56 of post 54 through channel 76 to insert post 54 into recess 74. Due to enlarged head 55 interacting with lip 75, post 54, and therefore lever 40, is prevented from moving in a direction along pivot axis P away from lever 60, but lever 40 and lever 60 can rotate relative to each other around pivot axis P. When joined together, levers 40,60 form a device 30 capable of applying a force to pull one bone anchor 10 toward another bone anchor 10, as discussed further below. FIG. 8 shows the assembled instrument 30 from a perspective normal to a theoretical plane P1 that is defined by axis L1 and pivot axis P (i.e., axis L1 and pivot axis P lie in plane P1—the plane of the paper). As can be seen in FIG. 8, axis L3 of the distal engaging section 64 of lever 60 diverges (in the generally distal direction) away from axis L1, with an angle β formed therebetween. In some embodiments, angle β may be approximately 10°-15°, such as about 12°. Of course, because axis L3 and axis L1 do not actually intersect, this is a projected angle. Further, another theoretical plane P2 is defined by axis L1 and axis L2. With reference to FIG. 8, this plane P2 is coming straight out of the paper. Note that pivot axis P is non-perpendicularly transverse to plane P2 at cant angle α (see FIG. 3), not perpendicular thereto as in a conventional scissor-type tool.

The surgical instrument 30 may be used to help assemble a spinal rod 20 to a plurality of anchor members 10 (e.g., polyaxial bone screws). For example, two anchoring members 10 are secured to respective vertebrae 5 of a spinal motion segment using any conventional method. A spinal rod 20 is inserted into the anchor members 10 using any conventional method. See, e.g., U.S. Pat. No. 7,465,306. The spinal rod 20 is affixed to one of the anchor members 10. For example, a setscrew 14 is tightened so that rod 20 is fixed relative to the anchor member 10 associated with the inferior vertebra 5, using known techniques. The rod 20 is advantageously not fixedly secured to the anchor member 10 associated with the superior vertebra 5, but is instead allowed to move relative thereto at this point in the procedure. The guide tube 41 of lever 40 is then slid over the head 12 of the superior anchor member 10 until the rod 20 rests in notches 46. Advantageously, the inner side of the guide tube 41, having the view port 47 therein, is oriented generally inferiorly, and the pivot axis P is oriented generally laterally. Lever 60 is then slid over the head 12 of the inferior anchor member 10 until the rod 20 rests in notches 66. During or after this, lever 60 is joined to lever 40 by sliding post 54 through channel 76 to recess 74. At this point, plane P2 is oriented generally parallel to the sagittal plane of the spine. The surgeon then moves (e.g. pulls) handle 42 toward handle 62 so as to pivot lever 40 relative to lever 60 and move distal engaging section 44 closer to distal engaging section 64. Due to the engagement of levers 40,60 to anchor members 10, this results in the anchor members 10 being moved toward each other, thereby moving rod 20 relative to the superior anchor member 10 and moving the vertebrae 5 closer together to compress the motion segment. At a desired amount of compression, a tightening tool 28 is inserted into bore 50 and used to tighten the setscrew 14 associated with the superior bone anchor 10 to affix the rod 20 relative to the superior bone anchor 10. Note that lever 40 acts as a counter-torque during this tightening process. Further, note that the presence of view ports 47, 67, if appropriately positioned, allow the distal ends of levers 40,60 to move closer together because the open "spaces" of the viewports 47,67 may overlap without hindering movement of the distal engaging sections 44, 64. The tightening tool 28 is then removed, lever 60 detached from lever 40 and inferior bone anchor 10, and then lever 40 detached from superior bone anchor 10. The surgical procedure then continues as is conventional.

While the discussion above has assumed that lever 40 is used with superior bone anchor 10 and lever 60 is used with inferior bone anchor 10, this could be reversed in some embodiments so that lever 60 is used with superior bone anchor 10 and lever 40 is used with inferior bone anchor 10. Likewise, while the discussion has assumed that the latter setscrew 14 to be tightened—resulting in rod 20 being fixedly secured to both bone anchors 10—is accessed via bore 50, this may be changed so that such setscrew 14 is instead accessed via bore 68 in lever 60, although such an approach is believed to be more cumbersome. Further, while it is assumed that one setscrew 14 is fully tightened before the instrument 30 is engaged to the bone anchors 10, the instrument 30 may, in some embodiments, be used to fully tighten both setscrews 14, with the setscrew 14 associated with lever 60 advantageously, but not necessarily, tightened fully before applying compression by pivoting levers 40,60 relative to each other.

In some embodiments, the instrument 30 may be used with conventional bone anchors 10 having a relatively constant height profile during installation. However, in some embodiments, the instrument 30 may be used with having so-called extended tabs. The tabs, indicated at 16 in FIG. 1, may be used during installation for providing additional travel to the setscrew 14 during tightening, as is known in the art. Such tabs 16 are typically broken off during the surgical procedure, after final tightening of the setscrew 14. See, e.g., U.S. Pat. No. 7,927,360. The distal engaging sections 44,64 may therefore advantageously be adapted to receive such tabs 16. For example, the bores 50, 68 may have non-circular cross-sections that allow for the tabs 16 to fit inside bores 50,68 without interference. Likewise, the bores 50,68 may be configured to allow for the use of extensions (not shown) that are sometimes used with such tabs 16 by being sized and shaped to receive the extensions. See U.S. patent application Ser. No. 12/913,371, which is incorporated herein by reference.

In some embodiments, the spinal rod 20 may be straight. In other embodiments, as discussed above, the spinal rod 20 may have a curvate longitudinal axis 22 that has a radius of curvature R. Advantageously, the distance D between the axis of rod 20 when disposed in notches 46,66 to the pivot axis P is approximately the same as R such that the center of curvature of the rod 20 is approximately, or advantageously precisely, disposed on pivot axis P.

In the discussion above, it has been assumed that the post 54 is associated with lever 40 and the recess 74 is associated with lever 60. However, this male/female relationship may be reversed in some embodiments. Likewise, the above discussion has assumed that mounting block 52 is distinct from guide tube 41, but affixed thereto. However, in some embodiments, mounting block 52 may be integral (i.e., monolithically formed) with guide tube 41. Similarly, the various portions of lever 60 may be distinct or integrally formed with the other portions in any suitable combination.

The discussion above has been in the context of the levers 40,60 being mated for pivoting action in releasable fashion via pin 54 and recess 74. However, in some embodiments, the levers 40,60 may be mated for pivoting action in non-releasable fashion, such as by insertion of a suitable pin through mounting block 72 against neck 56, closure of channel 76, or other means known in the art.

The various aspects of the surgical instrument 30, such as counter-torque action, optional releasable coupling of levers 40,60, co-planar action of handles 42,62, and other aspects, may be found individually in various embodiments of the surgical instrument 30, or in any combination. Further, while it is contemplated that the surgical instrument may be advantageously used for installation of spinal rod 20 from a posterior approach, other approaches, such as an anterior, lateral, oblique, or any other surgical approach, may alternatively be used.

The various patents and patent publications mentioned above are each incorporated herein by reference in their entirety.

The present invention may be carried out in other specific ways than those herein set forth without departing from the scope and essential characteristics of the invention. The present embodiments are, therefore, to be considered in all respects as illustrative and not restrictive, and all changes coming within the meaning and equivalency range of the appended claims are intended to be embraced therein.

What is claimed is:

1. A surgical instrument for assembling a spinal rod to a plurality of anchoring members comprising:
    the first lever comprising a hollow guide tube extending along a first longitudinal axis from a first proximal handle section to a first distal end section; the guide tube having a first longitudinal bore extending therethrough along the first axis; the first lever further comprising a first intermediate section disposed between the first handle section and the first distal end section;
    a second lever having a second proximal handle section, a second distal end section, and an intervening second intermediate section; the second handle section extending along a second longitudinal axis; the second distal end section extending along a third longitudinal axis; wherein the second and third axes are non-parallel;
    the second distal end section having a second longitudinal bore extending along the third axis;
    the first and second levers pivotally connected at the first and second intermediate sections for relative rotation about a pivot axis;
    the first and second axes extending in a common first plane;
    wherein the pivot axis is transverse to the first plane at a non-perpendicular first angle;
    wherein the third axis is transverse to the first plane at a non-perpendicular second angle;
    wherein pivoting of the second lever relative to the first lever about the pivot axis causes the second proximal end section to traverse along the first plane.

2. The surgical instrument of claim 1 wherein the first and second levers are removably and pivotally connected via a male protrusion protruding along the pivot axis and a female recess extending along the pivot axis.

3. The surgical instrument of claim 2 wherein the first lever comprises the male protrusion.

4. The surgical instrument of claim 1:
    wherein the first distal end section comprises a first end notch extending generally perpendicular to the first axis;
    wherein the second distal end section comprise a second end notch extending generally perpendicular to the third axis.

5. The surgical instrument of claim 1 wherein the second intermediate section comprises a curvate section that links the second distal end section to the second handle section in offset fashion.

6. The surgical instrument of claim 1 wherein the first and third axes intersect the pivot axis, and the second axis is skew relative to the pivot axis.

7. The surgical instrument of claim 1 wherein the first and second bores are non-circular in cross-section.

8. The surgical instrument of claim 1 wherein the first lever further comprises a first mounting block; said guide tube extending through the first mounting block at the first intermediate section.

9. The surgical instrument of claim 8 wherein the second intermediate section comprises a second mounting block; wherein the second mounting block comprises a recess extending along the pivot axis for receiving a portion of the first mounting block.

10. The surgical instrument of claim 9:
    wherein the first and second levers are removably and pivotally connected via the recess;
    wherein the second mounting block further comprises a channel extending radially outward relative to the pivot axis; the channel terminating in the recess on one end and at peripheral surface of the second mounting block on the opposing end.

11. The surgical instrument of claim 10 wherein the first mounting block comprises a protrusion extending along the pivot axis and configured to slide through the channel and into the recess to rotatably mount the first lever to the second lever.

12. The surgical instrument of claim 1 wherein the first and second levers are releasably and pivotally connected.

13. The surgical instrument of claim 1 further comprising a spinal rod coupled to the first and second distal end sections; wherein the spinal rod has a curvate longitudinal axis with a curvature generally centered on the pivot axis.

14. The surgical instrument of claim 1 wherein the first and second bores are configured to mate with bone screw assemblies having extended tabs.

15. A surgical instrument for assembling a spinal rod to a plurality of anchoring members comprising:
    a first lever comprising a hollow guide tube extending along a first longitudinal axis from a first proximal handle section to a first distal end section; the guide tube having a first longitudinal bore extending therethrough along the first axis; the first lever further comprising a first intermediate section disposed between the first handle section and the first distal end section;
    a second lever having a second proximal handle section, a second distal end section, and an intervening second intermediate section; the second handle section extending along a second longitudinal axis; the second distal end section extending along a third longitudinal axis; wherein the second and third axes are non-parallel;
    the second distal end section having a second longitudinal bore extending therethrough along the third axis;
    the first and second levers removably and pivotally connected at the first and second intermediate sections for relative rotation about a pivot axis; wherein the pivot axis is non-perpendicularly transverse to the first axis;

wherein the instrument is configured such that when viewed normal to a plane defined by the first axis and the pivot axis:
the first and third axes proximally diverge;
the first and second axes are parallel.

16. The surgical instrument of claim 15 wherein the first and second intermediate sections comprise a male protrusion protruding along the pivot axis and a female recess extending along the pivot axis, the male protrusion and the female recess releasably coupling the second lever to the first lever for rotation about the pivot axis.

17. The surgical instrument of claim 16 further comprising a channel extending radially outward relative to the pivot axis; the channel terminating in the recess on one end and at peripheral surface of the corresponding intermediate section on the opposing end; wherein the male protrusion is configured to slide through the channel and into the recess to rotatably mount the second lever to the first lever.

18. A method of assembling a spinal rod to a plurality of anchoring members comprising:
affixing a spinal rod at a first bone anchor anchored to a first vertebra;
engaging a first lever with a first bone anchor anchored to a first vertebra;
engaging a second lever with a second bone screw anchored to a second vertebra;
the first lever comprising a hollow guide tube extending along a first longitudinal axis from a first proximal handle section to a first distal end section; the guide tube having a first longitudinal bore extending therethrough along the first axis; the first lever further comprising a first intermediate section disposed between the first handle section and the first distal end section;
the second lever having a second proximal handle section, a second distal end section, and an intervening second intermediate section; the second handle section extending along a second longitudinal axis; the second distal end section extending along a third longitudinal axis; wherein the second and third axes are non-parallel;
removably coupling the second lever to the first lever at the first and second intermediate sections for relative rotation about a pivot axis; wherein the pivot axis is non-perpendicularly transverse to the first axis;
thereafter, moving the first and second bone anchors closer together by rotating the first lever relative to the second lever about the pivot axis;
while the first and second bone anchors are disposed closer together, affixing a spinal rod at the both the first and second bone anchors by tightening a fastener via the first or second bores;
thereafter, decoupling the first and second levers from each other and removing the first and second levers from the first and second bone anchors.

19. The method of claim 18 wherein the spinal rod has a curvate longitudinal axis with a curvature generally centered on the pivot axis during the rotating the first lever relative to the second lever about the pivot axis.

20. The method of claim 18 wherein, after the coupling the second lever to the first lever and during the rotating the first lever relative to the second lever about the pivot axis, the instrument is configured such that when viewed normal to a plane defined by the first axis and the pivot axis:
the first and third axes proximally diverge;
the first and second axes are parallel.

* * * * *